US006458986B1

United States Patent
Frutos et al.

(10) Patent No.: US 6,458,986 B1
(45) Date of Patent: Oct. 1, 2002

(54) INTERMEDIATE FOR (R)-3-(4-BROMOBENZYL)-1-(3,5-DICHLOROPHENYL)-5-IODO-3-METHYL-1-H-IMIDAZO[1,2-α]IMIDAZOL-2-ONE

(75) Inventors: Rogelio P. Frutos, Sandy Hook; Michael Dale Johnson, Danbury, both of CT (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 0 days.

(21) Appl. No.: 10/077,044

(22) Filed: Feb. 15, 2002

Related U.S. Application Data

(62) Division of application No. 09/918,915, filed on Jul. 31, 2001.
(60) Provisional application No. 60/224,166, filed on Aug. 9, 2000.

(51) Int. Cl.[7] ............................................. C07C 275/24
(52) U.S. Cl. ....................................................... 560/34
(58) Field of Search .......................................... 560/34

(56) References Cited

U.S. PATENT DOCUMENTS 5,484,802 A    1/1996 Patel et al.

FOREIGN PATENT DOCUMENTS

WO    WO 01 07440 A1    2/2001

OTHER PUBLICATIONS

Frutos, et al; "An improved synthesis of N–aryl–hydatoin LFA–1 antagonists via the enantiospecific alkylation of an isobutyraldehyde–derived imidazolidinone template", Tetrahedron: Asymmetry, 12 (2001) 101–104.

Appel, et al; "Notiz ueber eine neue Carbodiimid–Synthese", Chem. Ber. 104, 1335–1336 (1971).
Lee, et al, "The Reaction of Vinyl Phosphates with Iodothimethylsilane: Synthesis of Vinyl Iodides from Ketones", Tetrahedron Letters, vol. 34, No. 15, 2433–2436, 1993.
Nicolaou, et al, "Synthesis of N–heterocycles via lactam–derived ketene aminal phosphates. Asymmetric synthesis of cyclic amino acids.", Chem. Commun. 1998, 1757–1758.
Takahata, et al, "An Asymmetric Total Synthesis of (–)-Supinidine", Tetrahedron, vol. 47, No. 36, 7635–7644, 1991.
Williams, et al, "Carbodilmide Chemistry: Recent Advances", Chem. Rev.vol. 81, No. 4, 1981, 589–636.
Yee, "Self–Regeneration of Stereocenters: A Practical Enantiospecific Synthesis of LFA-1 Antagonist BIRT–377", Organic Letters, vol. 2, No. 18, 2000, 2781–2783.

*Primary Examiner*—Robert W. Rausuer
*Assistant Examiner*—Rebecca Anderson
(74) *Attorney, Agent, or Firm*—Robert P. Raymond; Philip I. Datlow; Alan R. Stempel

(57) ABSTRACT

A novel process for the preparation of (R)-3-(4-Bromobenzyl)-1-(3,5-dichlorophenyl)-5-iodo-3-methyl-1-H-imidazo[1,2-α]imidazol-2-one (1):

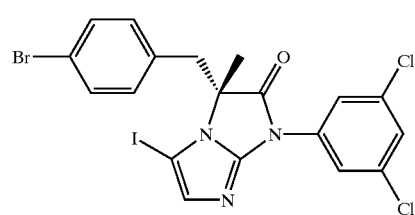

This compound is useful as an intermediate in the preparation of certain small molecules that are useful in the treatment or prevention of inflammatory and immune cell-mediated diseases. The present invention also relates to certain intermediates used in this novel process.

2 Claims, No Drawings

INTERMEDIATE FOR (R)-3-(4-BROMOBENZYL)-1-(3,5-DICHLOROPHENYL)-5-IODO-3-METHYL-1-H-IMIDAZO[1,2-α]IMIDAZOL-2-ONE

RELATED APPLICATIONS

This application is a divisional of U.S. application Ser. No. 09/918,915, filed on Jul. 31, 2001, which claims benefit to U.S. Provisional Application Ser. No. 60/224,166, filed on Aug. 9, 2000, both of which are herein incorporated by reference in their entirety.

FIELD OF THE INVENTION

The present invention relates generally to a novel process for the preparation of (R)-3-(4-Bromobenzyl)-1-(3,5-dichlorophenyl)-5-iodo-3-methyl-1-H-imidazo[1,2-α]imidazol-2-one. This compound is useful as an intermediate in the preparation of certain small molecules that are useful in the treatment or prevention of inflammatory and immune cell-mediated diseases. The present invention also relates to certain novel intermediates used in this novel process.

BACKGROUND OF THE INVENTION (R)-3-(4-Bromobenzyl)-1-(3,5-dichlorophenyl)-5-iodo-3-methyl-1-H-imidazo[1,2-α]-imidazol-2-one (1) is an advanced intermediate used in the preparation of certain small molecules that inhibit the interaction of cellular adhesion molecules, specifically by antagonizing the binding of human intercellular adhesion molecules (including ICAM-1, ICAM-2 and ICAM-3) to the Leukointegrins (especially CD18/CD11a or "LFA-1"). As a result, these small molecules are useful in the treatment or prevention of inflammatory and immune cell-mediated diseases. See U.S. application Ser. No. 09/604,312, Wu et al., filed on Jun. 27, 2000, herein incorporated by

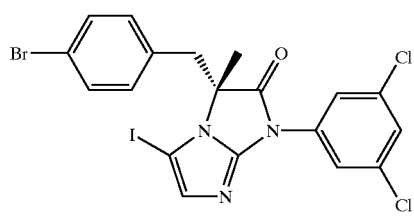

reference.

The method that has been used to prepare compound 1 is illustrated in Scheme 1 below.

Scheme 1

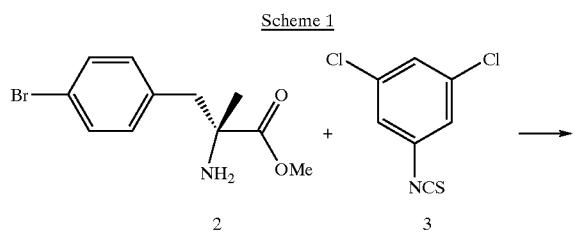

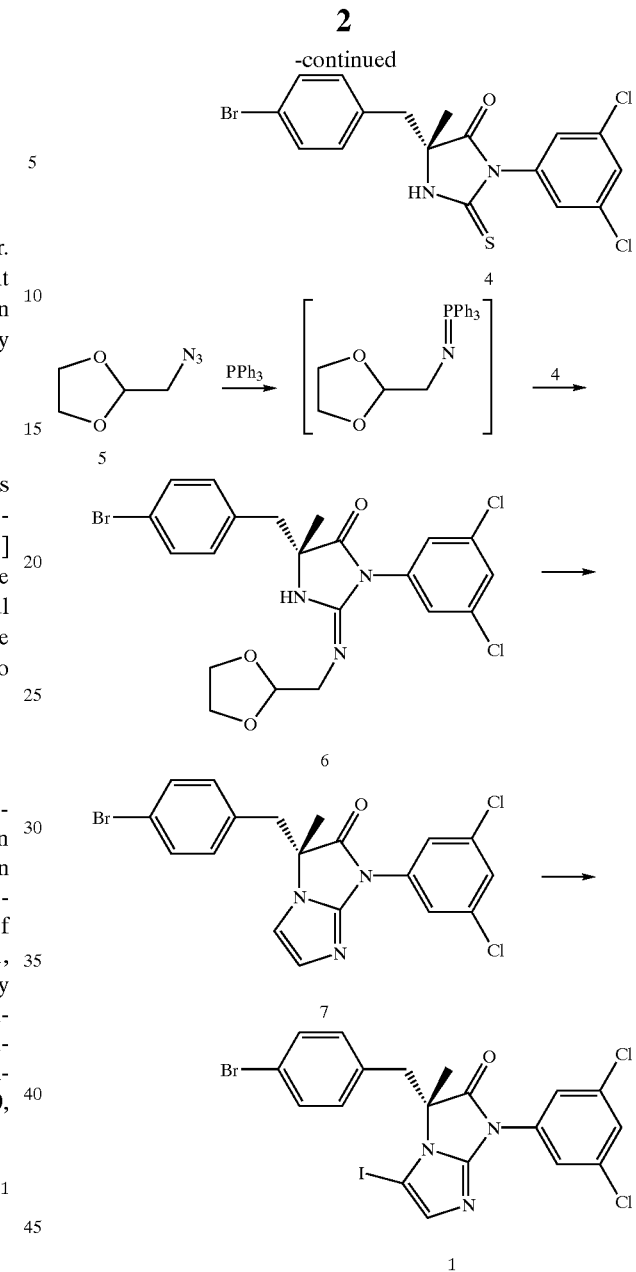

In this procedure, an amino-ester 2 was reacted with 3,5-dichlorophenylisothiocyanate 3 to provide thiohydantoin 4. To a solution of triphenylphosphine (PPh$_3$) was added the azide 5. After stirring at room temperature overnight, thiohydantoin 4 was added to provide 6. Treatment of 6 with trifluoroacetic acid provided 7. Iodination was then carried out by reaction of 7 with N-iodosuccinimide and pyridinium p-toluenesulfonate to provide 1. Recovered 7 may be recycled to provide additional 1.

SUMMARY OF THE INVENTION

The present invention is directed to a novel process for the preparation of compound 1. A first aspect of the invention is directed to a process for preparing a compound of the formula 1:

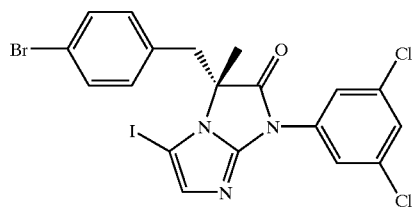

said process comprising the following steps:

a) reacting a compound of the formula I with a compound of the formula

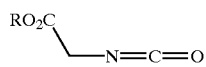

where R is $C_{1-6}$alkyl, in an aprotic organic solvent, followed by adding a triarylphosphine, a carbon tetrahalide and a tertiary amine, to form a compound of the formula IIa where R is $C_{1-6}$alkyl:

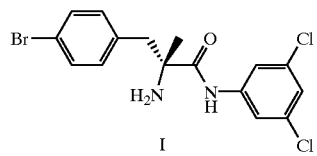 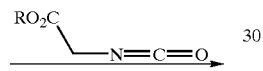

IIa b) optionally hydrolyzing a compound of the formula IIa produced in step a) by reacting the compound of formula IIa with a base to form a compound of the formula IIb:

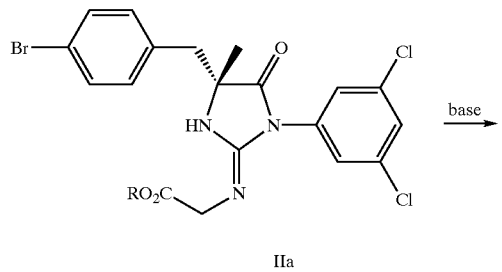

IIa

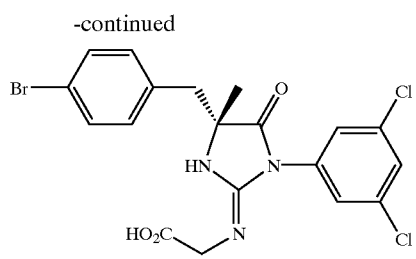

IIb c) reacting a compound of the formula IIa produced in step a) with a Lewis acid and a phosphine oxide compound of the formula $(R_1)_3PO$, wherein $R_1$ is $C_{1-6}$alkyl or aryl, in an aprotic organic solvent to form a compound of the formula III:

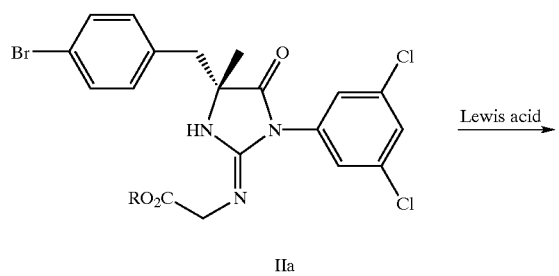

IIa

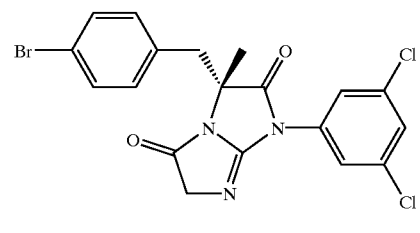

III or when the optional step b) is performed, reacting a compound of the formula IIb produced in step b) with a coupling agent in an aprotic organic solvent to form a compound of the formula III:

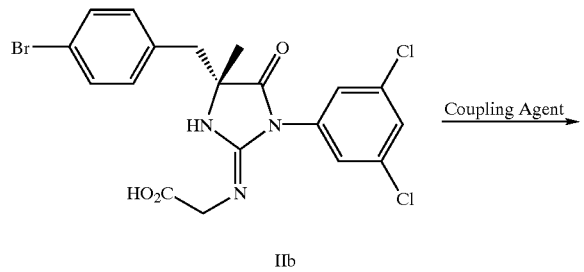

IIb

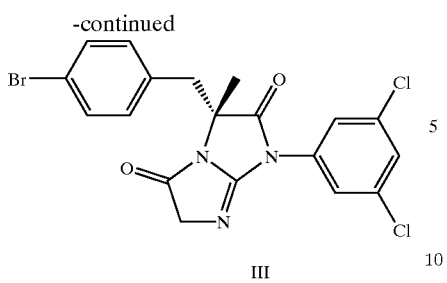

III d) reacting a compound of the formula III produced in step c) with a strong base and a compound of the formula $(R_2O)_2POCl$, wherein $R_2$ is $C_{1-6}$alkyl or aryl, in a polar organic solvent at a temperature of about −90° C. to about 0° C. to form a compound of the formula IV where $R_2$ is $C_{1-6}$alkyl or aryl:

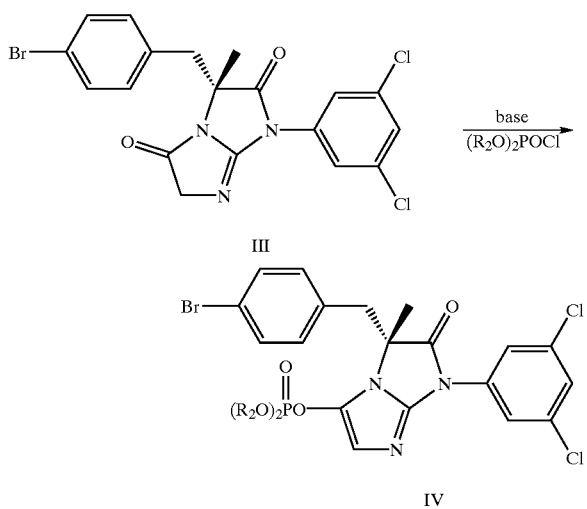

e) reacting a compound of the formula IV produced in step d) with trimethylsilyl iodide, or with sodium iodide and trimethylsilyl chloride, in an aprotic organic solvent to form a compound of the formula 1:

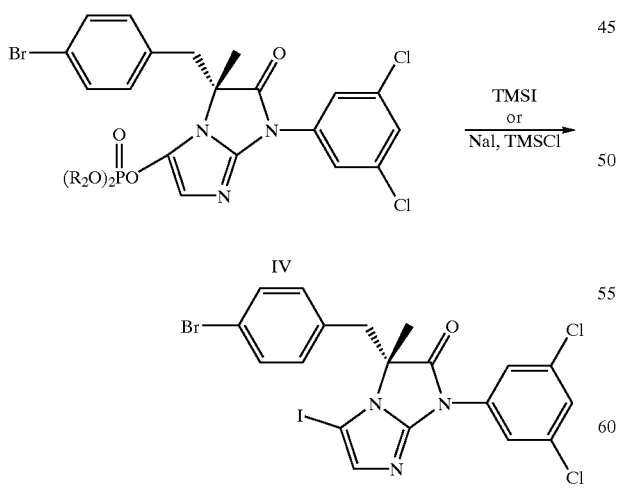

A second aspect of the invention is directed to the individual novel steps of the above inventive process. A third aspect of the invention is directed to the novel intermediates IIa, IIb, III and IV. A final aspect of the invention is directed to the novel urea intermediate of the following formula Ia produced in the first step of the inventive process and its process of preparation:

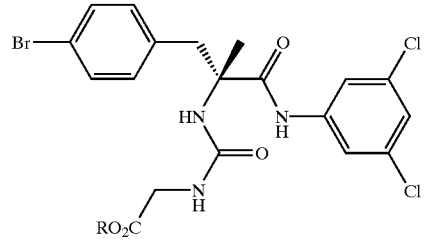

wherein R is $C_{1-6}$alkyl.

DETAILED DESCRIPTION OF THE INVENTION

The individual steps of the inventive process are described in detail below, along with other aspects of the present invention.

All terms as used herein in this specification, unless otherwise stated, shall be understood in their ordinary meaning as known in the art. For example, a "$C_{1-6}$alkyl" is an alkyl group having from 1 to 6 carbon atoms, which group can be branched or unbranched. The term "aryl", either alone or as part of another group, shall be understood to mean an optionally substituted 6–10 membered aromatic carbocycle; "aryl" includes, for example, phenyl and naphthyl, each of which may be optionally substituted.

Optimum reaction conditions and reaction times for the individual steps may vary depending on the particular reactants used. Unless otherwise specified, solvents, temperatures, pressures and other reaction conditions may be readily selected by one of ordinary skill in the art. Specific procedures are provided in the Synthetic Examples section. Typically, reaction progress may be monitored by thin layer chromatography (TLC) if desired. Intermediates and products may be purified by chromatography on silica gel and/or recrystallization. Unless otherwise set forth, the starting materials and reagents are either commercially available or may be prepared by one skilled in the art using methods described in the chemical literature.

Step (a)

Step a) of the inventive process comprises reacting a compound of the formula I with a compound of the formula

where R is $C_{1-6}$alkyl, in an aprotic organic solvent, followed by adding a triarylphosphine, a carbon tetrahalide and a tertiary amine, to form a compound of the formula IIa where R is $C_{1-6}$alkyl:

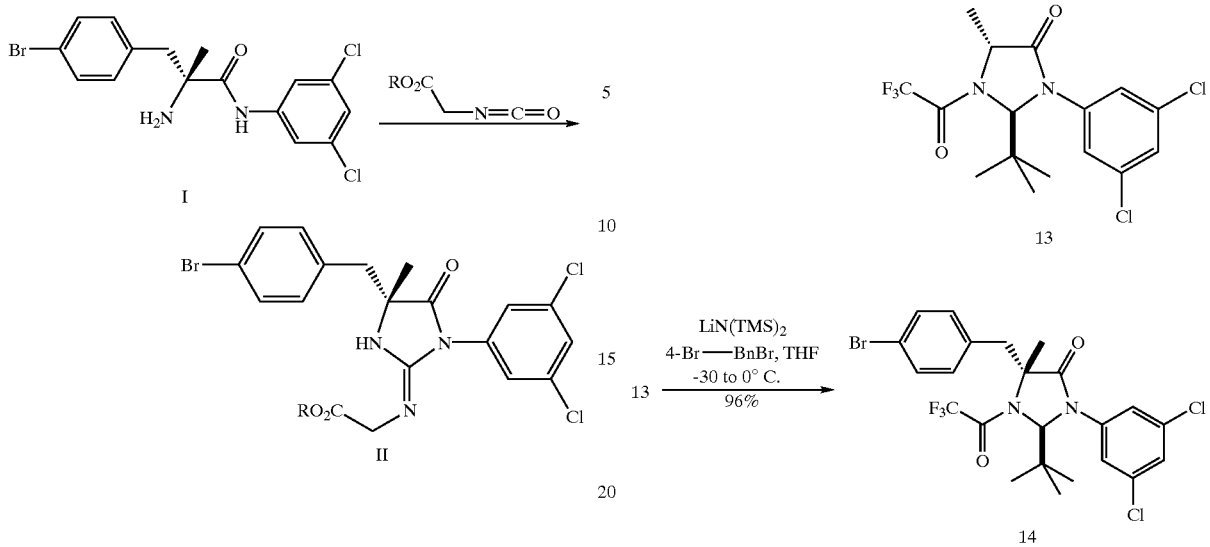

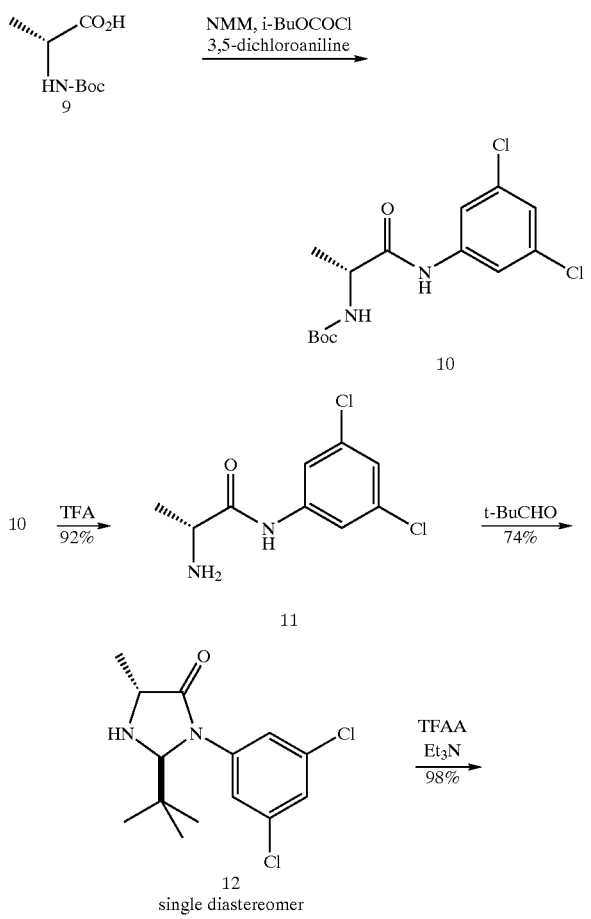

The starting material of formula I is prepared as described in Yee, N., "Self-Regeneration of Stereocenters: A Practical Enantiospecific Synthesis of LFA-1 Antagonist BIRT-377", Org. Lett. 2000, 2, 2781–2783, which is herein incorporated by reference in its entirety. This process is set forth in detail below:

The commercially available (D)-N-Boc-alanine 9 is reacted with 3,5-dichloroaniline via a mixed anhydride intermediate (i-BuOCOCl, N-methylmorpholine, −10° C. to rt, THF) to give amide 10. Deprotection of the crude amide 10 by TFA in dichloromethane afforded amino N-aryl amide 11 in 92% yield over two steps.

The amino amide 11 is treated with pivalaldehyde in refluxing pentane. A crystalline solid is directly formed from the reaction mixture and identified as the desired trans imidazolidinone 12 as a single diastereomer in 74% yield. After protection of 12 (TFAA, Et$_3$N, 0° C. to rt, CH$_2$Cl$_2$, 98% yield) to obtain 13, the crude 13 in THF is deprotonated with LiN(TMS)$_2$ at −30 to −20° C. and then the resulting enolate is alkylated at −30° C. to 0° C. with 4-bromobenzyl bromide from the opposite face of the t-butyl group to give the 5,5-disubstituted 14 as a single diastereomer in 96% yield.

The trifluoroacetamide group of 14 is first hydrolyzed (1.5 eq. BnMe$_3$NOH, 2.0 eq. 50% NaOH, rt to 40° C., dioxane) to give a mixture of the corresponding partially hydrolyzed N-unsubstituted acetal of 14, Schiff base of I, and I itself. Subsequent direct addition of 6N HCl to the above mixture resulted in complete hydrolysis to afford amino amide I in quantitative yield.

In step (a) of the present inventive process, the compound of formula I is first reacted with an isocyanatoacetate of the formula

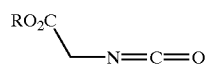

where R is C$_{1-6}$alkyl to form a urea of the following formula Ia in situ:

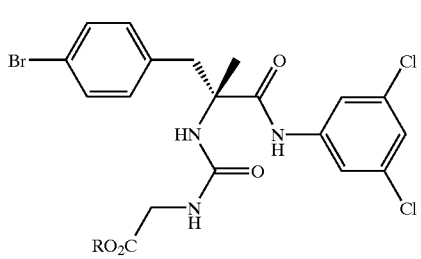

where R is $C_{1-6}$alkyl. It is not necessary to isolate the novel urea Ia, although it has been isolated and characterized. The urea of formula Ia is dehydrated in situ by adding a triarylphosphine, a carbon tetrahalide and a tertiary amine to the reaction mixture. The resulting carbodiimide undergoes a spontaneous cyclization to provide the ester of formula IIa in good yield.

The formation of ureas from isocyanates in general is documented in the scientific literature (See, e.g., *Chem. Rev.* 1981, 589, and references cited therein). In the process of the present invention, however, it is not necessary to isolate the urea, which can be dehydrated in situ to afford a carbodiimide that further undergoes a spontaneous cyclization.

The dehydration of a urea to afford an intermediate carbodiimide is also documented in the literature (Appel, R., Kleinstuck, R., Ziehn, K. *Chem. Ber.* 1971, 104, 1335). However, the process of the present invention goes beyond the dehydration of the urea intermediate, since the carbodiimide is not isolated and undergoes a spontaneous cyclization to give IIa.

Moreover, the novel compound of formula IIa is another aspect of the present invention and is not disclosed in the above cited references.

Suitable $C_{1-6}$alkyl R groups for the isocyanatoacetate and formula IIa in step a) include, for example, methyl and ethyl.

Step a) is performed in an aprotic organic solvent. Suitable aprotic organic solvents for this step include, for example, tetrahydrofuran, toluene, dichloromethane, dichloroethane and chloroform. Suitable triarylphosphines in step a) include, for example, triphenylphosphine, wherein the phenyl groups are optionally substituted, for example, with one or more methoxy or amino groups. Suitable carbon tetrahalides in step a) include, for example, $CCl_4$ and $CBr_4$. Suitable tertiary amines in step a) include, for example, trialkylamine, 1-methylpyrrolidine or 1-methylmorpholine. A preferred tertiary amine for use in step a) is triethylamine.

Step (b)

Step (b) of the inventive process is an optional hydrolysis step and comprises hydrolyzing the ester compound of the formula IIa produced in step a) by reacting the compound of formula IIa with a base to form the corresponding acid compound of the formula IIb:

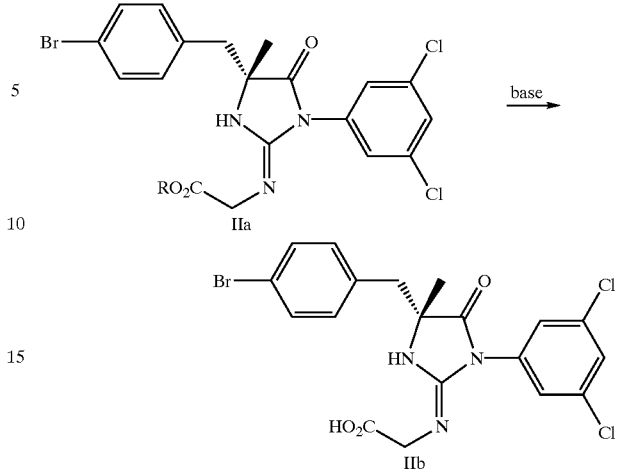

Suitable bases for this step include, for example, alkali metal hydroxides such as lithium hydroxide, sodium hydroxide or potassium hydroxide. The novel compound of formula IIb produced in this step is another aspect of the present invention.

In one embodiment of the inventive process, this optional hydrolysis step b) is not performed and the ester of formula IIa produced in step a) is used directly in the next step of the process, step c).

Step (c)

Step (c) of the inventive process comprises reacting a compound of the formula IIa produced in step a) with a Lewis acid and a phosphine oxide compound of the formula $(R_1)_3PO$, wherein $R_1$ is $C_{1-6}$alkyl or aryl, in an aprotic organic solvent to form a compound of the formula III:

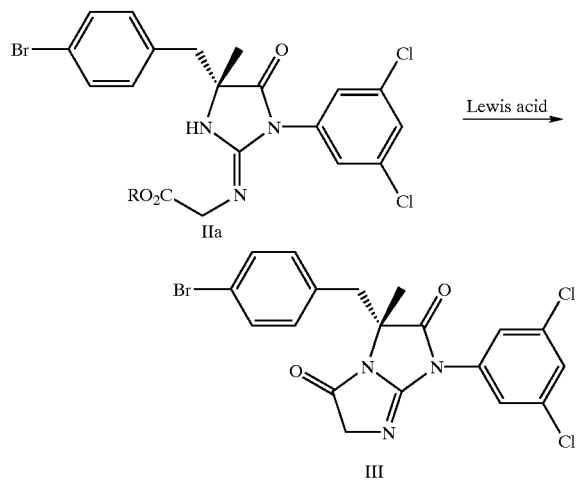

or when the optional step b) is performed, step c) comprises reacting a compound of the formula IIb produced in step b) with a coupling agent in an aprotic organic solvent to form a compound of the formula III:

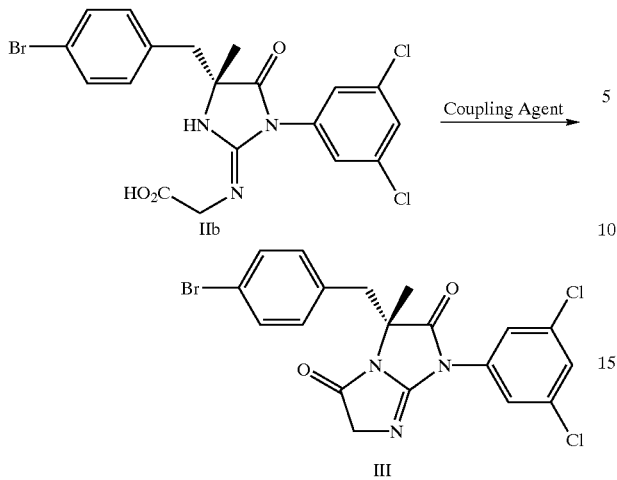

IIb

III

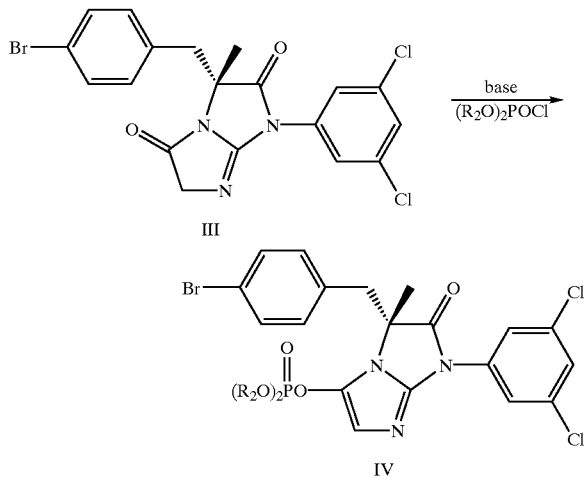

III

IV

When the ester compound of formula IIa employed in step (c), the ester IIa is cyclized in the presence of a Lewis acid and a phosphine oxide compound to provide the imidazo-imidazole-3,5-dione of formula III in good yield. This is similar to a known procedure for the synthesis of lactams (Takahata, H., Banba, Y., Momose, T. *Tetrahedron*, 1991, 47, 7635). It was observed, however, that following the reaction conditions described in the literature failed to afford the desired product III in significant yield. It was discovered that the addition of a phosphine oxide compound of the formula $(R_1)_3PO$, wherein $R_1$ is $C_{1-6}$alkyl or aryl, was necessary for the reaction to proceed efficiently.

Step c) is performed in an aprotic organic solvent. Suitable aprotic organic solvents for this step include, for example, tetrahydrofuran, toluene, dichloromethane, dichloroethane or chloroform. Suitable Lewis acids for use in this step include, for example, $AlCl_3$, $TiCl_4$ and trialkylaluminums of the formula $(C_{1-6}alkyl)_3Al$, such as $Me_3Al$. Suitable phosphine oxides for this step include, for example, triarylphosphine oxides such as triphenylphosphine oxide, wherein the phenyl groups are optionally substituted with one or more methoxy or amino groups.

When the acid compound of formula IIb is employed in step (c), a coupling agent is used to cause cyclization via an intramolecular coupling between the carboxylic acid group and the amine group (i.e., a peptide-type coupling reaction). Suitable coupling agents for this purpose include conventional peptide coupling agents, for example, acetic anhydride, acetyl chloride, thionyl chloride and oxalyl chloride. Suitable aprotic organic solvents for this step are the same as described above.

The novel imidazo-imidazole-3,5-dione compound of formula III produced in step c) is another aspect of the present invention.

Step (d)

Step (d) of the inventive process comprises reacting a compound of the formula III produced in step c) with a strong base and a compound of the formula $(R_2O)_2POCl$, wherein $R_2$ is $C_{1-6}$alkyl or aryl, in a polar organic solvent at a temperature of about $-90°$ C. to about $0°$ C. to form a compound of the formula IV where $R_2$ is $C_{1-6}$alkyl or aryl:

The synthesis of the vinyl phosphate compound IV is similar to a known procedure for the preparation of ketene aminal phosphates from lactams (Nicolau, K. C., Shi, G., Kenji, N., Bemal, F. *Chem. Commun.* 1998, 1757).

The novel vinyl phosphate compound of formula IV produced in step d) is another aspect of the present invention and is not disclosed by the above cited reference.

Step d) is conducted in the presence of a strong base. In the context of this invention, a strong base is a base having a pKa of greater than 20. Suitable strong bases for use in this step include, for example, alkali metal amides, such as potassium bis(trimethylsilyl)amide, lithium bis(trimethylsilyl)amide, sodium bis(trimethylsilyl)amide and lithium diisopropylamide.

In one embodiment, the $R_2$ group in the chlorophosphate compound $(R_2O)_2POCl$ and in the ompound of formula IV is a $C_{1-6}$alkyl group, preferably methyl or ethyl.

Step d) is conducted in a polar organic solvent. Suitable polar organic solvents include, for example, diethyl ether, dipropyl ether, diisopropyl ether, dibutyl ether, methyl tert-butyl ether (MTBE), dipentyl ether, diisopentyl ether, ethylene glycol dimethyl ether, diethylene glycol dimethyl ether, dioxane, tetrahydrofuran, N,N-dimethylformamide, N,N-dimethyl-acetamide, DMSO or N-methyl-2-pyrollidone.

Step d) is conducted at a temperature of about $-90°$ C. to about $0°$ C., preferably about $-50°$ C. to about $-5°$ C., more preferably about $-30°$ C. to about $-10°$ C. In one embodiment, step d) is conducted at a temperature of about $-20°$ C. The term "about" in this context means a temperature between 10% above and 10% below the recited value, inclusive. For example, "about $-20°$ C." means a temperature falling in the range $-18°$ C. to $-22°$ C.

Step (e)

Step (e) of the inventive process is an iodination that comprises reacting a compound of the formula IV produced in step d) with trimethylsilyl iodide (TMSI), or with sodium iodide (Na) and trimethylsilyl chloride (TMSCl), in an aprotic organic solvent to form a compound of the formula 1:

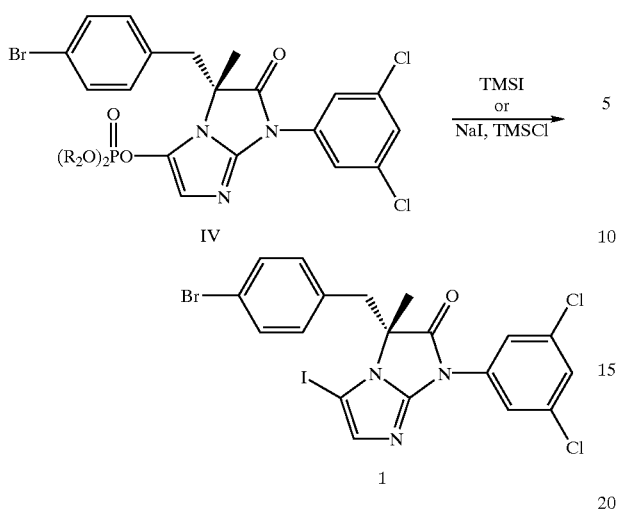

The synthesis of the compound of formula 1 from the vinyl phosphate compound of formula IV is related to a known procedure for the preparation of vinyl iodides from ketone-derived enol phosphates (Lee, K., Wiemer, D. F. *Tetrahedron Lett.* 1993, 34, 2433).

However, the enol phosphates in the literature procedure are ketone-derived vinyl phosphates and not lactam-derived ketene aminal phosphates like formula IV.

The iodination in step e) is conducted by reacting the vinyl phosphate compound of formula IV with trimethylsilyl iodide, or with sodium iodide and trimethylsilyl chloride. When sodium iodide and trimethylsilyl chloride are used, these two compounds react in situ to form trimethylsilyl iodide, which then reacts with formula IV to form the iodinated compound of formula 1.

Step e) is conducted in an aprotic organic solvent. Suitable aprotic organic solvents for this step include, for example, tetrahydrofuran, toluene, dichloromethane, dichloroethane, chloroform and acetonitrile.

Step (e) is optionally conducted in the presence of water. It has been found that water accelerates the formation of the iodide compound of formula 1. This step has been run with up to 6 equivalents of water, although higher amounts of water can be used. In one embodiment, the amount of water present is from about 0.5 to 1.5 equivalents, preferably about 0.8 to 1.2 equivalents.

SYNTHETIC EXAMPLES

The invention is further illustrated by the following non-limiting examples of the inventive process.

Example 1

(R){3-[2-(4-Bromophenyl)-1-(3,5-dichlorophenylcarbamoyl)-1-methyl-ethyl]-ureido}-acetic Acid Ethyl Ester Ethyl isocyanatoacetate (80.7 mL, 719 mmol) was added dropwise to a stirred solution of I (281 g, 698 mmol) and THF (2 L) at ambient temperature. The mixture was stirred at room temperature for 12 h and hexane (600 mL) was added. The resulting solid was collected by filtration. The filtrate was concentrated under reduced pressure and the resulting precipitate was again collected by filtration. The solid material was combined to afford a total of 325 g of product as a white solid: $^1$H NMR (400 MHz, (D$_3$C)$_2$SO) δ 1.17 (t, J=7.1 Hz, 3H), 1.23 (s, 3H), 3.05 (d, J=13.3 Hz, 1H), 3.29 (d, J=13.3 Hz, 1H), 3.75 (dd, J=6.0 Hz, J=17.7 Hz, 1H), 3.84 (dd, J=6.0, J=17.7 Hz, 1H), 4.10 (q, J=7.1 Hz 2H), 6.35 (s, 1H), 6.40 (t, J=6.0 Hz, 1H), 7.10 (d, J=8.2 Hz, 2H), 7.23 (t, J=1.8 Hz, 1H), 7.44 (d, J=8.2 Hz, 2H), 7.74 (d, J=1.8 Hz, 2H), 9.83 (s, 1H).

Example 2

(R)-[4-(4-Bromobenzyl)-1-(3,5-dichlorophenyl)-4-methyl-5-oxo-imidazolidin-2-ylideneamino]-acetic Acid Ethyl Ester Method A:

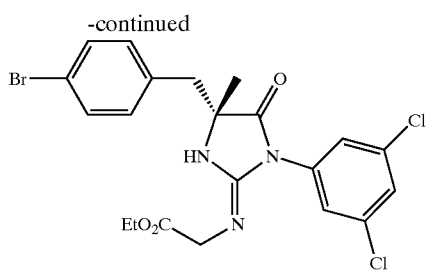

Carbon tetrachloride (43.6 mL, 452 mmol) was added dropwise to a stirred solution of the product of Example 1 (120 g, 226 mmol), triethylamine (63.0 mL, 452 mmol), triphenylphosphine (119 g, 452 mmol) and dichloromethane (1.8 L) at room temperature. The mixture was stirred at ambient temperature for 12 h and concentrated under reduced pressure. Ethyl acetate (1.2 L) was added and the mixture was stirred for 5–10 min. The solids were removed by filtration and the organic layer was washed sequentially with 0.5 N HCl (450 mL) and saturated aqueous NaHCO$_3$ (450 mL). The mixture was concentrated under reduced pressure to afford an orange oil. Ethyl acetate (240 mL) was added to the mixture at 50° C. followed by MTBE (720 mL) and the mixture was stirred at 60° C. for a few min. The mixture was allowed to reach ambient temperature and was stirred for 12 h. The precipitate (triphenylphosphine oxide) was then removed by filtration and the filtrate was concentrated under reduced pressure to afford 134 g of an orange solid. $^1$H NMR analysis of the crude material indicated it contained about 38% w/w triphenylphosphine oxide. A small sample was purified by chromatography for analytical purposes and the bulk of the material was used for the next step without further purification.

Method B:

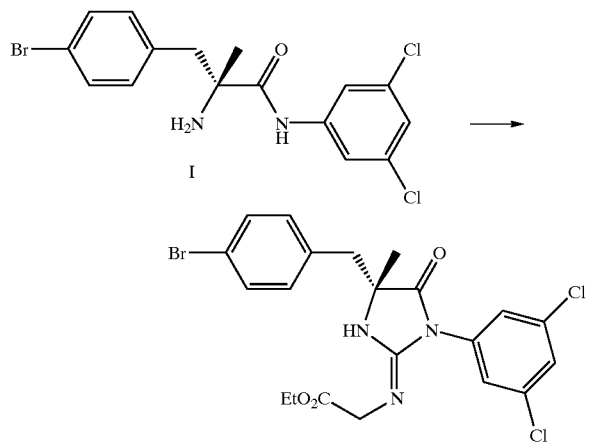

Ethyl isocyanatoacetate (0.287 mL, 2.56 mmol) was added dropwise to a stirred solution of I (1.0 g, 2.49 mmol) and dichloromethane (5 mL) at room temperature. The mixture was stirred for 10 min at room temperature and the urea (product of Example 1) forms as a white precipitate. Stirring was continued for about 2 h thereafter to ensure complete conversion to the urea, and then triphenylphosphine (1.31 g, 4.98 mmol), triethylamine (0.69 mL, 4.98 mmol), and carbon tetrachloride (0.48 mL, 4.98 mmol) were added to the stirred suspension. The mixture was then stirred at ambient temperature for 12 h. Aqueous workup (1 N HCl, dichloromethane, MgSO$_4$) afforded a yellow oil. Flash chromatography (silica gel, 4:1 hexane/ethyl acetate v/v) afforded 906 mg (71%) of product as a white solid: mp 103–105° C.; $^1$H NMR (400 MHz, CDCl$_3$) δ 1.31 (t, J=7.1 Hz, 3H), 1.52 (s, 3H), 2.95 (d, J=12.9 Hz, 1H), 2.98 (d, J=12.9 Hz, 1H), 4.05–4.13 (m, 3H), 4.23 (m, 2H), 6.57 (d, J=1.6 Hz, 2H), 7.04 (d, J=8.2 Hz, 2H), 7.37 (m, 3H); $^{13}$C NMR (CDCl$_3$, 100 MHz) δ 14.1, 23.7, 42.9, 44.2, 61.7, 70.4, 120.9, 125.6, 129.4, 130.8, 131.9, 133.2, 134.8, 136.1, 151.1, 169.6, 181.5; Anal. calcd for C$_{21}$H$_{20}$BrCl$_2$N$_3$O$_3$: C, 49.15; H, 3.93; N, 8.19. Found C, 49.46; H, 3.92; N, 7.96.

Example 3

(R)-3-(4-Bromobenzyl)-1-(3,5-dichlorophenyl)-3-methyl-1,6-dihydroimidazo[1,2-a]imidazole-2,5-dione

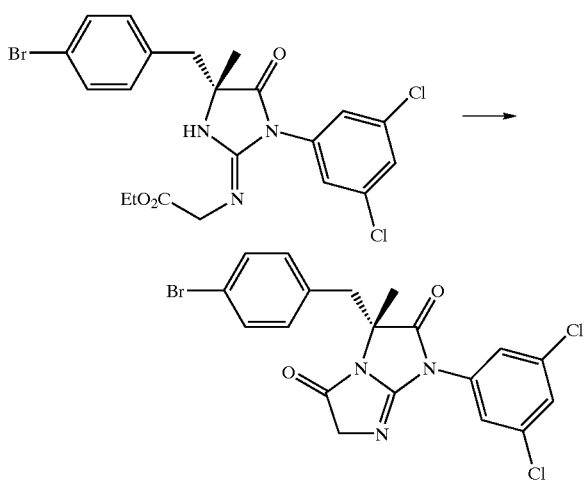

Toluene (450 mL) was added to 76.9 g of a mixture of the product of Example 2 (47.1 g, 91.7 mmol) and triphenylphosphine oxide (29.2 g, 105 mmol), and the resulting solution was cooled down to −10° C. Trimethylaluminum (46 mL of a 2 M solution in toluene, 92 mmol) was added dropwise keeping the temperature at or below 0° C. and the mixture was then allowed to reach ambient temperature. The mixture was stirred at ambient temperature for two h and more trimethylaluminum (27.6 mL of a 2 M solution in toluene, 55.2 mmol) was added in two portions at two h intervals. The mixture was placed over an ice bath and slowly quenched with 1 N HCl (360 mL). The organic portion was separated and the aqueous portion was extracted with toluene (200 mL). The combined organic portions were washed with water and concentrated under reduced pressure to afford an orange oil. Flash chromatography (silica gel, hexane/ethyl acetete 4:1 v/v) afforded 38.1 g (89%) of product as an oil that solidified upon standing: mp 52–54° C.; $^1$H NMR (400 MHz, CDCl$_3$) δ 1.84 (s, 3H), 3.24 (d, J=13.8 Hz, 1H), 3.43 (d, J=13.8 Hz, 1H), 4.18 (d, J=21.9 Hz, 1H), 4.30 (d, J=21.9 Hz, 1H), 6.95 (d, J=8.3 Hz, 2 H), 7.29 (d, J=1.8 Hz 2H), 7.33 (t, J=1.8 Hz, 1H), 7.38 (d, J=8.3 Hz, 2H); $^{13}$C NMR (100 MHz, CDCl$_3$)δ 21.5, 40.8, 61.3, 65.1, 122.3, 122.6, 128.5, 131.0, 132.0, 132.5, 132.7, 135.5, 154.6, 174.3, 174.9; Anal. calcd for C$_{19}$H$_{14}$BrC$_{12}$N$_3$O$_2$: C, 48.85; H, 3.02; N, 9.00. Found C, 48.89; H, 3.02; N, 8.81.

Example 4

Phosphoric Acid (R) 5-(4-Bromobenzyl)-7-(3,5-dichlorophenyl)-5-methyl-6-oxo-6,7-dihydro-5H-imidazo[1,2-α]imidazol-3-yl Ester Diethyl Ester

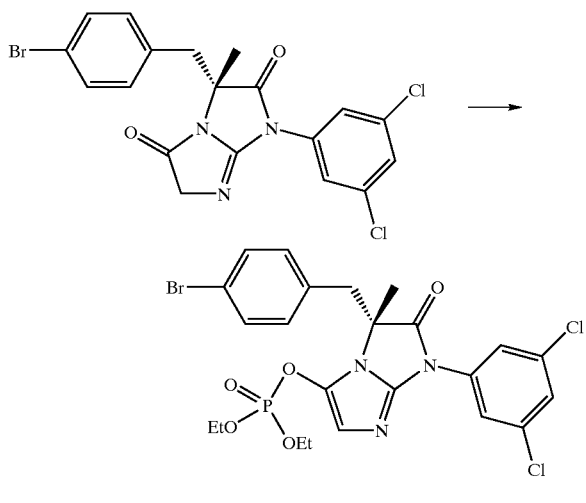

Potassium bis(trimethylsilyl)amide (265 mL of a 0.5 M solution in toluene, 133 mmol) was added dropwise to a stirred solution of the product of Example 3 (51.5 g, 110.3 mmol), diethyl chlorophosphate (23.9 mL, 165 mmol) and THF (700 ml) at −20° C. The mixture was stirred at −20° C. for one h. Aqueous workup (aqueous NH$_4$Cl, ethyl acetate, MgSO$_4$) afforded an oil. Flash chromatography (silica gel, hexane/ethyl acetate 2:1 v/v) afforded 61.2 g (92%) of product as a yellow oil: $^1$H NMR (400 MHz, CDCl$_3$) δ 1.44 (t, J=7.1 Hz, 6H), 1.86 (s, 3H), 3.26 (d, J=13.9 Hz), 3.34 (d, J=13.9 Hz, 1H), 4.33 (m, 4H), 6.50 (s, 1H), 6.84 (d, J=8.2 Hz, 2H), 7.24–7.28 (m, 3H), 7.58 (d, J=1.6 Hz, 2H).

Example 5

(R)-3-(4-Bromobenzyl)-1-(3,5-dichlorophenyl)-5-iodo-3-methyl-1H-imidazo[1,2-α]imidazol-2-one

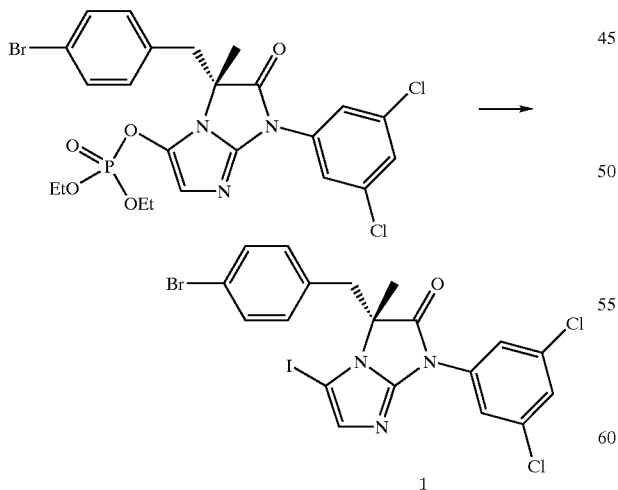

Trimethylsilyl chloride (42.8 mL, 338 mmol) was added dropwise to a stirred suspension of NaI (49.5 g, 330 mmol), the product of Example 4 (66.3 g, 110 mmol) and dichloromethane (1.1 L) at −10° C. The mixture was allowed to reach ambient temperature and stirred for 90 min. The mixture was placed over an ice bath and quenched with a mixture of saturated aqueous NaHCO$_3$ solution (360 mL) and 10% aqueous sodium thiosulfate (360 mL). The organic layer was set aside and the aqueous layer was extracted with dichloromethane (500 mL). The combined organic portions were dried (MgSO$_4$) and concentrated to afford 100 g of a light brown oil. Flash chromatography (silica gel, 6:1 hexane/ethyl acetate v/v) afforded 44.1 g (69%) of product as a colorless solid: $^1$H NMR (400 MHz, CDCl$_3$) δ 1.92 (s, 3H), 3.24 (d, J=14 Hz, 1H), 3.54 (d, J=14 Hz, 1H), 6.78 (d, J=8.3 Hz, 2H), 6.95 (s, 1H), 7.27 (m, 3H), 7.53 (d, J=1.8 Hz, 2H).

What is claimed is:

1. A compound having the following formula Ia:

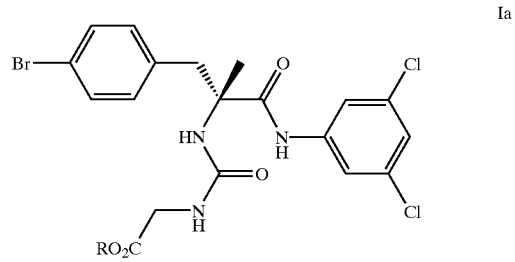

wherein R is C$_{1-6}$alkyl.

2. A process for preparing a compound of claim 1 having the formula Ia, said process comprising reacting a compound of the formula I with a compound of the formula

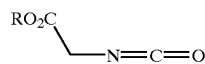

where R is C$_{1-6}$alkyl, in an aprotic organic solvent, to form a compound of the formula Ia where R is C$_{1-6}$alkyl:

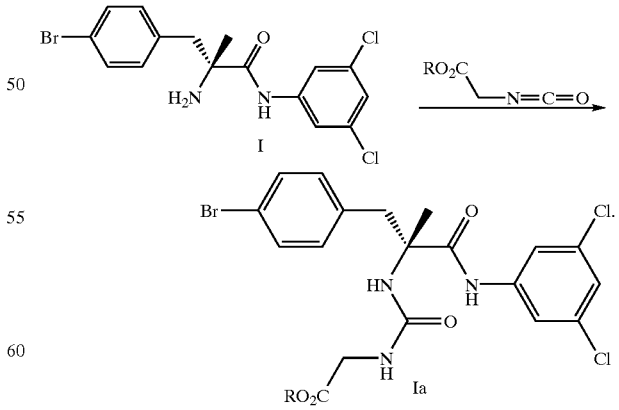

* * * * *